United States Patent [19]

Clason et al.

[11] 4,263,150

[45] Apr. 21, 1981

[54] PHOSPHITE TREATMENT OF PHOSPHORUS ACID SALTS AND COMPOSITIONS PRODUCED THEREBY

[75] Inventors: Donald L. Clason, Mentor; Calvin W. Schroeck, Eastlake, both of Ohio

[73] Assignee: The Lubrizol Corporation, Wickliffe, Ohio

[21] Appl. No.: 47,534

[22] Filed: Jun. 11, 1979

[51] Int. Cl.$^3$ .................. C10M 1/48; C10M 3/42; C10M 5/24; C10M 7/46
[52] U.S. Cl. .................. 252/32.7 E; 252/32.7 R; 260/429 K; 260/429 R; 260/429.7; 260/429.9; 260/430; 260/431; 260/435 R; 260/438.1; 260/439 R; 260/448 R
[58] Field of Search .................. 260/429.9, 448 R, 430, 260/438.1, 431, 429.7, 439 R, 435 R, 429 R, 429 K; 252/32.7 E, 32.7 R

[56] References Cited

U.S. PATENT DOCUMENTS

| | | | |
|---|---|---|---|
| 3,361,667 | 1/1968 | Wenborne et al. | 252/32.7 E |
| 3,489,682 | 1/1970 | Lesuer | 252/32.7 |
| 4,158,633 | 6/1979 | Papay | 252/32.7 E |

FOREIGN PATENT DOCUMENTS 2204701 8/1973 Fed. Rep. of Germany ...... 252/32.7 E

*Primary Examiner*—Helen M. S. Sneed
*Attorney, Agent, or Firm*—Daniel N. Hall; William H. Pittman; Raymond F. Keller

[57] ABSTRACT

The properties of salts of dialkylphosphorodithioic acids are improved by treating said salts or their acid precursors with phosphites, especially triaryl phosphites. This process reduces the tendency of the salts to stain and corrode metal parts, especially copper parts, when incorporated in lubricants and functional fluids. The process may also be used to treat mixed metal salts of dialkylphosphorodithioic and carboxylic acids.

22 Claims, No Drawings

PHOSPHITE TREATMENT OF PHOSPHORUS ACID SALTS AND COMPOSITIONS PRODUCED THEREBY

This invention relates to a method for preparing phosphorus acid salt compositions of improved properties, to compositions prepared by the method, and to lubricants and functional fluids containing such compositions. In its broadest sense, the invention is a method for improving the properties of salts of phosphorus acids of the formula $(RO)_2PSSH$, wherein each R is independently a hydrocarbon-based radical, which comprises contacting said salts or their phosphorus acid precursors with at least one phosphite of the formula $(R'O)_3P$, wherein each R' is independently hydrogen or a hydrocarbon-based radical and at most one R' is hydrogen, at a temperature between about 50° and about 200° C.

The use of metal salts, especially zinc salts, of phosphorodithioic acids as antioxidants and extreme pressure agents in lubricants and functional fluids has been known for some time. However, the environment in which such lubricants and functional fluids are used has become increasingly severe over recent years with the further development of machinery employing such lubricants and functional fluids. A problem frequently encountered in recent years is corrosive attack and staining of metal (especially copper) parts in machinery by the lubricant.

The usual method for the preparation of phosphorodithioic acid salts involves a first step of reacting at least one alcohol or phenol with phosphorus pentasulfide to form the free acid, and a second step of neutralizing the acid with a metal base to form the desired salt. In this procedure, it is sometimes advantageous to use phosphorus pentasulfide containing somewhat in excess of the stoichiometric amount of sulfur. For example, a product having improved filterability is obtained by the use of phosphorus pentasulfide which, instead of containing only the stoichiometric 72.1% sulfur by weight, contains up to about 73% and typically about 72.3–72.7% sulfur. The advantages of the resulting product are, however, accompanied by disadvantages in that the excess sulfur remains in the phosphorodithioic acid salt and causes the aforementioned corrosion and staining.

A principal object of the present invention, therefore, is to provide a method for the production of phosphorodithioic acid salts having improved properties.

A further object is to produce phosphorodithioic acid salts which are less corrosive to metal parts, especially copper parts, then the salts previously obtained by the use of phosphorus pentasulfide containing an excess of sulfur.

A further object is to provide improved phosphorodithioic acid salts and lubricants or functional fluids containing them.

Other objects will in part be obvious and will in part appear hereinafter.

The present invention is based on the discovery that corrosiveness of the above-described phosphorus acid salts to copper is materially decreased by contacting said salts or their phosphorus acid precursors with at least one phosphite compound having the above formula. The term "hydrocarbon-based radical", as used in connection with the definition of R' in that formula, denotes a radical having a carbon atom directly attached to the remainder of the molecule and having predominantly hydrocarbon character within the context of this invention. Such radicals include the following:

(1) Hydrocarbon radicals; that is, aliphatic, (e.g., alkyl or alkenyl), alicyclic (e.g., cycloalkyl or cycloalkenyl), aromatic (which are preferred), aliphatic- and alicyclic-substituted aromatic, aromatic-substituted aliphatic and alicyclic radicals. Such radicals are known to those skilled in the art; examples include methyl, ethyl, butyl, cyclohexyl, phenyl, tolyl, phenethyl and biphenylyl (all isomers being included).

(2) Substituted hydrocarbon radicals; that is, radicals containing non-hydrocarbon substituents which, in the context of this invention, do not alter the predominantly hydrocarbon character of the radical. Those skilled in the art will be aware of suitable substituents (e.g., halo, hydroxy, alkoxy, carbalkoxy, nitro, alkylsulfoxy).

(3) Hetero radicals; that is, radicals which, while predominantly hydrocarbon in character within the context of this invention, contain atoms other than carbon present in a chain or ring otherwise composed of carbon atoms. Suitable hetero atoms will be apparent to those skilled in the art and include, for example, nitrogen, oxygen and sulfur.

In general, no more than about three substituents or hetero atoms, and preferably no more than one, will be present for each 10 carbon atoms in the hydrocarbon-based radical.

Preferably, the hydrocarbon-based radicals present as R' in the phosphite compound are free from acetylenic and usually also from ethylenic unsaturation and have from about 1 to about 12 carbon atoms, desirably up to about 10 carbon atoms. The radicals are usually hydrocarbon and especially lower hydrocarbon, the word "lower" denoting radicals containing up to seven carbon atoms. They are preferably lower alkyl or aryl radicals, most often lower aryl and especially phenyl.

As is apparent from the definition of the phosphite herein, it may be tertiary or secondary. That is, it may contain three or only two (respectively) hydrocarbon-based radicals per molecule. Secondary phosphites are generally considered to have a tautomeric structure:

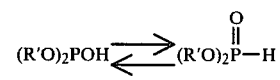

The tertiary phosphites are preferred for use in the method of this invention.

The phosphorus acids which may be treated (or their salts treated) according to the method of this invention, are, as previously indicated, those of the formula $(RO)_2PSSH$ wherein each R is independently a hydrocarbon-based radical and usually a hydrocarbon radical. The R radicals are preferably free from acetylenic and usually also from ethylenic unsaturation and generally have from about 3 to about 50 carbon atoms, especially from about 3 to about 18 carbon atoms. Alkyl radicals, particularly branched chain alkyl radicals, are preferred. The salts are usually those of metals including the Group I metals, Group II metals, aluminum, tin, cobalt, lead, molybdenum, manganese and nickel, as well as mixtures thereof. The preferred salts are those of zinc.

As previously mentioned, the phosphite treatment may be effected either on the free phosphorus acid or on its salt. It is usually more convenient, and is frequently preferred, to treat the salt.

It is also within the scope of the invention to treat mixed salts of the above-described phosphorus acids and at least one carboxylic acid with phosphites. The carboxylic acid may be monocarboxylic or polycarboxylic; monocarboxylic acids are preferred, especially those of the formula R"COOH wherein R" is an aliphatic or alicyclic hydrocarbon-based radical. R" is most often a hydrocarbon radical, generally an alkyl radical and preferably a branched chain alkyl radical. It usually contains from about 2 to about 40 and especially from about 4 to about 20 carbon atoms. Such mixed metal salts may be prepared by blending metal salts of the phosphorus and carboxylic acids or by neutralizing a mixture of the acids with at least one metal base. Frequently a stoichiometric excess of the metal base (e.g., up to about 2 and especially up to about 1.5 equivalents per equivalent of acid) may be used. The ratio of equivalents of phosphorus acid to carboxylic acid may be from about 0.1:1 to about 30:1, preferably from about 0.5:1 to about 20:1.

The method of this invention is conveniently effected by merely heating the phosphorus acid salt with the phosphite compound at a temperature typically between about 50° and about 200° C. and preferably between about 100° and about 150° C. The reaction may be carried out in a substantially inert, normally liquid organic diluent such as mineral oil, xylene or the like; if the diluent is mineral oil or is physically and chemically similar to mineral oil, it frequently need not be removed before using the product in a lubricant or functional fluid. The amount of phosphite used is generally between about 2 and about 20 parts, preferably between about 2 and about 10 parts, by weight per 100 parts of salt. If the free phosphorus acid is treated with the phosphite, the weight proportions thereof are adjusted to be equivalent to the desired level of treatment of the salt.

The method of this invention is illustrated by the following examples. All parts and percentages are by weight.

EXAMPLES 1-14

Triphenyl phosphite is heated with a zinc dialkylphosphorodithioate or a mixed zinc salt of a dialkylphosphorodithioic acid and a carboxylic acid. The dialkylphosphorodithioic acid used in the preparation of the zinc salt is itself prepared by the reaction of at least one alcohol with phosphorus pentasulfide which contains a stoichiometric excess of sulfur. The reaction conditions and results are given in Table I. Examples 1-11 relate to the phosphite treatment of zinc dialkylphosphorodithioates, and Examples 12-14 to mixed zinc salts of dialkylphosphorodithioic and carboxylic acids. The salts used in Examples 12-14 are prepared by reacting zinc oxide with 4 equivalents of the dialkylphosphorodithioic acid and 1 equivalent of the carboxylic acid, a total of 1.3 equivalents of zinc oxide being used per equivalent of acid. The reactions are carried out in a small amount of mineral oil as diluent.

TABLE I

| Example | R | R" | % S in $P_2S_5$ | Parts $(C_6H_5O)_3P$ per 100 parts salt | Temp., °C. | Time, hrs. |
|---|---|---|---|---|---|---|
| 1 | 80% 2-ethylhexyl, 20% isobutyl | — | 72.6 | 3.5 | 120 | 4 |
| 2 | 80% 2-ethylhexyl, 20% isobutyl | — | 72.6 | 7.5 | 120 | 4 |
| 3 | 2-Ethylhexyl | — | 72.3 | 2.5 | 120 | 4 |
| 4 | 2-Ethylhexyl | — | 72.3 | 3.5 | 120 | 4 |
| 5 | 2-Ethylhexyl | — | 72.3 | 7.5 | 120 | 4 |
| 6 | Isohexyl | — | 72.3–72.7 | 3.5 | 120 | 4 |
| 7 | Isohexyl | — | 72.3–72.7 | 7.5 | 120 | 4 |
| 8 | Isooctyl | — | 72.3–72.7 | 2.5 | 120 | 4 |
| 9 | Isooctyl | — | 72.3–72.7 | 3.5 | 120 | 4 |
| 10 | Isooctyl | — | 72.3–72.7 | 7.5 | 120 | 4 |
| 11 | 65% t-butyl, 35% isoamyl | — | 72.3–72.7 | 7.5 | 120 | 4 |
| 12 | 2-Ethylhexyl | 3-Heptyl | 72.6 | 3.4 | 120 | 3 |
| 13 | 2-Ethylhexyl | 3-Heptyl | 72.3–72.7 | 6.5 | 130 | 3½ |
| 14 | 2-Ethylhexyl | 3-Heptyl | 72.3–72.7 | 7.5 | 130 | 4 |

EXAMPLE 15

A dialkylphosphorodithioic acid composition is prepared by the reaction of phosphorus pentasulfide containing 72.3–72.7% sulfur with a mixture of 80 mole percent 2-ethylhexanol and 20 mole percent butanol. To 1006 parts of the acid is added 43 parts of triphenyl phosphite and the mixture is heated for one hour at 110° C.

The phosphite-treated acid composition is added over 30 minutes to a suspension of 139 parts of zinc oxide in 121 parts of mineral oil. The temperature increases to 64° C. during the addition. The mixture is heated to 80° C. for 3 hours, vacuum stripped and filtered using a filter aid material to yield the desired zinc salt as an approximately 90% solution in mineral oil.

As previously indicated, the compositions of this invention are useful as additives for lubricants and functional fluids, in which they function primarily as antioxidants and extreme pressure agents having a decreased tendency to corrode or stain metals as compared with ordinary phosphorodithioic acid salts. They can be empolyed in a variety of lubricants based on diverse oils of lubricating viscosity, including natural and synthetic lubricating oils and mixtures thereof. The lubricants include crankcase lubricating oils for spark-ignited and compression-ignited internal combustion engines, including automobile and truck engines, two-cycle engines, aviation piston engines, marine and railroad diesel engines, and the like. Also contemplated are lubricants for gas engines, stationary power engines and turbines and the like. Transaxle lubricants, gear lubricants, metal-working lubricants and other lubricating oil and grease compositions, as well as functional fluids such as hydraulic fluids and automatic transmission fluids, benefit from the incorporation therein of the compositions of the present invention.

Natural oils include animal oils and vegetable oils (e.g., castor oil, lard oil) as well as liquid petroleum oils and solvent-treated or acid-treated mineral lubricating oils of the paraffinic, naphthenic or mixed paraffinic-naphthenic types. Oils of lubricating viscosity derived from coal or shale are also useful base oils. Synthetic oils include hydrocarbon oils and halo-substituted hydrocarbon oils such as polymerized and interpolymerized olefins [e.g., polybutylenes, polypropylenes, propyleneisobutylene copolymers, chlorinated polybutylenes, poly(1-hexenes), poly(1-octenes), poly(1-decenes), etc. and mixtures thereof]; alkylbenzenes [e.g., dodecylbenzenes, tetradecylbenzenes, dinonylbenzenes, di(2-ethylhexyl)benzenes, etc.]; polyphenyls (e.g., biphenyls, terphenyls, alkylated polyphenyls, etc.), alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc. constitute another class of known synthetic oils. These are exemplified by the oils prepared through polymerization of ethylene oxide or propylene oxide, the alkyl and aryl ethers of these polyoxyalkylene polymers (e.g., methyl-polyisopropylene glycol ether having an average molecular weight of 1000, diphenyl ether of polyethylene glycol having a molecular weight of 500–1000, diethyl ether of polypropylene glycol having a molecular weight of 1000–1500, etc.) or mono- and polycarboxylic esters thereof, for example, the acetic acid esters, mixed $C_3$–$C_8$ fatty acid esters, or the $C_{13}$ Oxo acid diester of tetraethylene glycol.

Another suitable class of synthetic oils comprises the esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid, and the like.

Esters useful as synthetic oils also include those made from $C_5$ to $C_{12}$ monocarboxylic acids and polyols and polyol ethers such neopentyl glycol, trimethylolpropane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another useful class of synthetic oils [e.g., tetraethyl silicate, tetraisopropyl silicate, tetra(2-ethylhexyl) silicate, tetra-(4-methyl-2-ethylhexyl) silicate, tetra-(p-tert-butylphenyl) silicate, hexa-(4-methyl-2-pentoxy)-disiloxane, poly(methyl)-siloxanes, poly(methylphenyl)siloxanes, etc.]. Other synthetic oils include liquid esters of phosphorus-containing acids (e.g., tricresyl phosphate, trioctyl phosphate, diethyl ester of decylphosphonic acid, etc.), polymeric tetrahydrofurans and the like.

Unrefined, refined and rerefined oils (and mixtures of each with each other) of the type disclosed hereinabove can be used in the lubricants and functional fluids of the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be an unrefined oil. Refined oils are similar to the unrefined oils except they have been further treated in one or more purification steps to improve one or more properties. Many such purification techniques are known to those of skill in the art such as solvent extraction, acid or base extraction, filtration, percolation, etc. Rerefined oils are obtained by processes similar to those used to obtain refined oils applied to refined oils which have been already used in service. Such rerefined oils are also known as reclaimed or reprocessed oils and often are additionally processed by techniques directed to removal of spent additives and oil breakdown products.

Generally, the lubricants and functional fluids of the present invention contain an amount of the composition of this invention sufficient to provide it with antioxidant and improved extreme pressure properties. Normally this amount will be about 0.25% to about 10%, preferably about 0.5% to about 7.5%, of the total weight of the fluid.

The invention also contemplates the use of other additives in combination with the compositions of this invention. Such additives include, for example, detergents and dispersants of the ash-producing or ashless type, corrosion- and auxiliary oxidation-inhibiting agents, pour point depressing agents, auxiliary extreme pressure agents, color stabilizers and anti-foam agents.

The ash-producing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt" is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature above 50° C. and filtering the resulting mass. The use of a "promoter" in the neutralization step to aid the incorporation of a large excess of metal likewise is known. Examples of compounds useful as the promoter include phenolic substances such as phenol, naphthol, alkylphenol, thiophenol, sulfurized alkylphenol, and condensation products of formaldehyde with a phenolic substance; alcohols such as methanol, 2-propanol, octyl alcohol, cellosolve, carbitol, ethylene glycol, stearyl alcohol, and cyclohexyl alcohol; and amines such as aniline, phenylenediamine, phenothiazine, phenyl-β-naphthylamine, and dodecylamine. A particularly effective method for preparing the basic salts comprises mixing an acid with an excess of a basic alkaline earth metal neutralizing agent and at least one alcohol promoter, and carbonating the mixture at an elevated temperature such as 60°–200° C.

Ashless detergents and dispersants are so called despite the fact that, depending on its constitution, the dispersant may upon combustion yield a non-volatile material such as boric oxide or phosphorus pentoxide; however, it does not ordinarily contain metal and therefore does not yield a metal-containing ash on combustion. Many types are known in the art, and any of them are suitable for use in the lubricants of this invention. The following are illustrative:

(1) Reaction products of carboxylic acids (or derivatives thereof) containing at least about 34 and preferably at least about 54 carbon atoms with nitrogen-containing compounds such as amine, organic hydroxy compounds such as phenols and alcohols, and/or basic inorganic materials. Examples of these "carboxylic dispersants" are described in British Pat. No. 1,306,529 and in many U.S. patents including the following U.S. Pat Nos.:

3,163,603
3,184,474
3,215,707
3,219,666
3,271,310
3,272,746
3,281,357
3,306,908
3,311,558
3,316,177
3,340,281
3,341,542
3,346,493
3,351,552
3,381,022
3,399,141
3,415,750
3,433,744
3,444,170
3,448,048
3,448,049
3,451,933
3,454,607
3,467,668
3,501,405
3,522,179
3,541,012
3,542,678
3,542,680
3,567,637
3,574,101
3,576,743
3,630,904
3,632,510
3,632,511
3,697,428
3,725,441
Re 26,433

(2) Reaction products of relatively high molecular weight aliphatic or alicyclic halides with amines, preferably polyalkylene polyamines. These may be characterized as "amine dispersants" and examples thereof are described for example, in the following U.S. Pat. Nos.:

3,275,554
3,438,757
3,454,555
3,565,804

(3) Reaction products of alkyl phenols in which the alkyl group contains at least about 30 carbon atoms with aldehydes (especially formaldehyde) and amines (especially polyalkylene polyamines), which may be characterized as "Mannich dispersants". The materials described in the following U.S. Pat. Nos. are illustrative:

3,413,347
3,697,574
3,725,277
3,725,480
3,726,882

(4) Products obtained by post-treating the carboxylic, amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. Pat. Nos.:

3,036,003
3,087,936
3,200,107
3,216,936
3,254,025
3,256,185
3,278,550
3,280,234
3,281,428
3,282,955
3,312,619
3,366,569
3,367,943
3,373,111
3,403,102
3,442,808
3,455,831
3,455,832
3,493,520
3,502,677
3,513,093
3,533,945
3,539,633
3,573,010
3,579,450
3,591,598
3,600,372
3,639,242
3,649,229
3,649,659
3,658,836
3,697,574
3,702,757
3,703,536
3,704,308
3,708,522

(5) Interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates. These may be characterized as "polymeric dispersants" and examples thereof are disclosed in the following U.S. Pat. Nos.:

3,329,658
3,449,250

3,519,565
3,666,730
3,687,849
3,702,300

The above-noted patents are incorporated by reference herein for their disclosures of ashless dispersants.

Auxiliary extreme pressure agents and corrosion- and auxiliary oxidation-inhibiting agents are exemplified by chlorinated aliphatic hydrocarbons such as chlorinated wax; organic sulfides and polysulfides such as benzyl disulfide, bis(chlorobenzyl)disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate; phosphorus esters including principally dihydrocarbon and trihydrocarbon phosphites such as dibutyl phosphite, diheptyl phosphite, dicyclohexyl phosphite, pentylphenyl phosphite, dipentylphenyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutyl-substituted phenyl phosphite; and metal thiocarbamates, such as zinc dioctyldithiocarbamate and barium heptylphenyl dithiocarbamate.

The compositions of this invention can be added directly to the lubricant. Often, however, they are preferably diluted with a substantially inert, normally liquid organic diluent such as mineral oil, naphtha, benzene, toluene or xylene, to form an additive concentrate. These concentrates usually contain from about 20% to about 90% by weight of the salt of this invention and may contain, in addition, one or more other additives known in the art or described hereinabove.

In Table II are listed exemplary lubricants (Example C) and hydraulic fluids (Examples A and B) of this invention.

TABLE II

| Ingredient | Example | Parts by weight | | |
|---|---|---|---|---|
| | | A | B | C |
| Mineral oil | | 98.99 | 98.96 | 94.25 |
| Product of Example 11 | | — | 1.00 | — |
| Product of Example 12 | | 0.97 | — | 1.50 |
| Pentaerythritol ester of polybutenyl (mol.wt. about 1000) succinic acid, reacted with alkylene polyamine | | — | — | 1.43 |
| Reaction product of alkylene polyamine with polybutenyl (mol.wt. about 1700) succinic anhydride containing more than one succinic group per polybutenyl group | | — | — | 1.25 |
| Basic magnesium petroleum sulfonate | | — | — | 0.39 |
| Basic sulfurized calcium tetrapropenyl phenate | | — | — | 1.18 |
| Oxypropylated tetrapropenyl succinic acid | | 0.038 | 0.04 | — |
| Polyoxyalkylene demulsifier | | 0.0015 | — | — |
| Silicone anti-foam agent | | — | — | 0.01 |

What is claimed is:

1. A method for improving the properties of excess sulfur-containing salts of phosphorus acids of the formula $(RO)_2PSSH$, wherein each R is independently a hydrocarbon-based radical, which comprises contacting said salts or their phosphorus acid precursors under reaction conditions with at least one phosphite of the formula $(R'O)_3P$, wherein each R' is a hydrocarbon-based radical, at a temperature between about 50° and about 200° C.

2. A method according to claim 1 wherein each R' is an aromatic hydrocarbon radical.

3. A method according to claim 2 wherein each R is an alkyl radical having from about 3 to about 50 carbon atoms, the temperature is between about 80° and about 150° C., and the phosphite is contacted with said salt.

4. A method according to claim 3 wherein each R contains from about 3 to about 18 carbon atoms.

5. A method according to claim 4 wherein each R is a branched chain radical.

6. A method according to claim 5 wherein each R' is phenyl.

7. A method according to claim 6 wherein the salt is a zinc salt.

8. A method according to claim 1 wherein the salt is a mixed salt of at least one of said phosphorus acids and at least one carboxylic acid.

9. A method according to claim 8 wherein the carboxylic acid has the formula R"COOH wherein R" is an aliphatic or alicyclic hydrocarbon-based radical containing from about 2 to about 40 carbon atoms.

10. A method according to claim 9 wherein each R' is an aromatic hydrocarbon radical.

11. A method according to claim 10 wherein each R is an alkyl radical having from about 3 to about 50 carbon atoms and wherein the temperature is between about 80° and about 150° C., and the phosphite is contacted with said salt.

12. A method according to claim 11 wherein each R contains from about 3 to about 18 carbon atoms.

13. A method according to claim 12 wherein each R is a branched chain radical.

14. A method according to claim 13 wherein each R' is phenyl.

15. A method according to claim 14 wherein the salt is a zinc salt.

16. A method according to claim 13 wherein R" is an alkyl radical containing from about 4 to about 20 carbon atoms.

17. A method according to claim 16 wherein each R' is phenyl.

18. A method according to claim 17 wherein the salt is a zinc salt.

19. A method according to claim 18 wherein R is the 2-ethylhexyl radical and R" is the 3-heptyl radical.

20. A composition prepared by a method according to any one of claims 1–19.

21. An additive concentrate comprising a substantially inert, normally liquid organic diluent and a composition according to claim 20.

22. A lubricant or functional fluid comprising a major amount of a lubricating oil and a minor amount of a composition according to claim 20.

* * * * *